(12) United States Patent
Sasaki et al.

(10) Patent No.: US 9,820,791 B2
(45) Date of Patent: Nov. 21, 2017

(54) METHODS OF FILLING BONE USING BONE CEMENT MIXING AND DELIVERY DEVICES

(71) Applicant: Kyphon SARL, Neuchatel (CH)

(72) Inventors: Neil S. Sasaki, San Jose, CA (US); Samuel Lee, San Francisco, CA (US); Ankit K. Mehta, Santa Clara, CA (US); Craig E. Lauchner, Mountain View, CA (US)

(73) Assignee: Kyphon SÀRL, Neuchâtel (CH)

( * ) Notice: Subject to any disclaimer, the term of this patent is extended or adjusted under 35 U.S.C. 154(b) by 599 days.

(21) Appl. No.: 14/466,464

(22) Filed: Aug. 22, 2014

(65) Prior Publication Data

US 2016/0051301 A1    Feb. 25, 2016

(51) Int. Cl.
    *A61B 17/88*    (2006.01)

(52) U.S. Cl.
    CPC .......... *A61B 17/8816* (2013.01); *A61B 17/88* (2013.01); *A61B 17/8802* (2013.01); *A61B 17/8805* (2013.01); *A61B 17/8811* (2013.01); *A61B 17/8819* (2013.01); *A61B 17/8822* (2013.01); *A61B 17/8833* (2013.01); *A61B 2017/8838* (2013.01)

(58) Field of Classification Search
    CPC . A61B 17/88; A61B 17/8802; A61B 17/8805; A61B 17/8811; A61B 17/8816; A61B 17/8819; A61B 17/8822; A61B 17/8833; A61B 2017/8838
    See application file for complete search history.

(56) References Cited

U.S. PATENT DOCUMENTS

| | | | |
|---|---|---|---|
| 4,767,026 A | 8/1988 | Keller et al. | |
| 5,047,031 A | 9/1991 | Constantz | |
| 5,525,148 A | 6/1996 | Chow et al. | |
| 5,650,108 A | 7/1997 | Nies et al. | |
| 5,795,922 A | 8/1998 | Demian et al. | |
| 5,820,632 A | 10/1998 | Constantz et al. | |
| 6,083,264 A | 7/2000 | Wood et al. | |
| 6,302,574 B1 * | 10/2001 | Chan | A61B 17/8825 222/137 |
| 6,479,565 B1 | 11/2002 | Stanley | |
| 6,547,866 B1 | 4/2003 | Edwards et al. | |
| 7,135,027 B2 * | 11/2006 | Delmotte | A61B 17/8816 606/92 |

(Continued)

*Primary Examiner* — Larry E Waggle, Jr.

(57) ABSTRACT

Methods of filling bone cavities are provided. The methods use a bone cement mixing and delivery device that includes a shaft extending along an axis from a first end to a second end and including a passageway. The first end includes an adapter having a first opening that is in communication with the passageway. The second end includes a second opening that is in communication with the passageway. The shaft includes a mixing portion between the first and second ends. A connector includes a central portion that that is coupled to the adapter. The central portion includes a channel that is in communication with the first opening. The connector includes first and second ports that extend from the central portion. The first port includes a first lumen that is in communication with the channel. The second port includes a second lumen that is in communication with the channel.

14 Claims, 5 Drawing Sheets

(56) References Cited

U.S. PATENT DOCUMENTS

| | | | |
|---|---|---|---|
| 7,842,040 B2* | 11/2010 | Rabiner | A61B 17/7097 |
| | | | 606/92 |
| 8,357,147 B2* | 1/2013 | Burkinshaw | A61B 17/00491 |
| | | | 604/181 |
| 2005/0197422 A1 | 9/2005 | Mayadunne et al. | |
| 2006/0095138 A1 | 5/2006 | Truckai et al. | |
| 2006/0122614 A1 | 6/2006 | Truckai et al. | |
| 2006/0122625 A1 | 6/2006 | Truckai et al. | |
| 2008/0172059 A1 | 7/2008 | Trieu et al. | |
| 2011/0106054 A1* | 5/2011 | Osborne | A61B 17/8816 |
| | | | 604/518 |

* cited by examiner

METHODS OF FILLING BONE USING BONE CEMENT MIXING AND DELIVERY DEVICES

FIELD

The present disclosure generally relates to methods of using medical devices for bone repair, and more particularly to methods for mixing and dispensing bone cement or other materials.

BACKGROUND

Many medical procedures employ medical grade cement in connection with the restoration and strengthening of bone structures. During such procedures, cement is typically dispensed to a bone to fill in voids or spaces in the bone or between medical devices or implants attached to or embedded within the bone. These dispensing devices may include devices as simple as syringes and as complex as electronically controlled valves.

Due to the medical nature of some procedures, the amount and placement of the flowable cement in some situations may need to be administered under pressure. For example, some bone cements are highly viscous and require significant pressure to expel the bone cement from a dispensing device, such as, for example, a syringe. Despite the simplicity or complexity of the dispensing device, control over when, where, how much and at what pressure cement is dispensed is of concern. Currently, there is a need for a mixing and delivery device for cement that utilizes pressure to mix and deliver cement and would permit for fewer steps or less complicated steps in dispensing the flowable cement to the target tissue site, such as a bone cavity (e.g., bone void, bone defect, bone fracture, etc.). This disclosure describes improvements over these prior art technologies.

SUMMARY

The bone cement mixing and delivery device provided allows mixing of flowable components and then delivery of the bone cement without transfer to a separate mixing device. The bone cement mixing and delivery device provided, in some embodiments, comprises a sealed delivery device that allows a portion of the flowable bone cement to be dispensed by controlled delivery in multiple doses to various target tissue sites without the need to reload new bone cement in the device. In some embodiments, the bone cement mixing and delivery device provided allows an unlimited working time for the physician to apply the bone cement to the target tissue site. In some embodiments, the bone cement mixing and delivery device provided increases physician safety by decreasing the radiation exposure as the bone cement mixing and delivery device, in some embodiments, is a sufficient length (e.g., at least 48 inches) to keep the physician out of the fluoroscopic field.

In one exemplary embodiment, there is a method of filling a bone cavity with a bone cement, the method, comprising: filling the bone cavity with the bone cement delivered from a bone mixing and delivery device having an elongated shaft extending along a longitudinal axis from a first end to a second end and comprising an inner surface defining a passageway, the first end comprising an adapter comprising an inner surface defining a first opening that is in communication with the passageway, the second end comprising a second opening that is in communication with the passageway, the shaft comprising a mixing portion between the first and second ends; and a connector comprising a central portion that that is coupled to the adapter, the central portion comprising an inner surface defining a channel that is in communication with the first opening, the connector comprising first and second ports that extend from the central portion, the first port comprising an inner surface defining a first lumen that is in communication with the channel, the second port comprising an inner surface defining a second lumen that is in communication with the channel.

In another exemplary embodiment, there is a method of filling a bone cavity with a bone cement, the method comprising: filling the bone cavity with the bone cement delivered from a bone mixing and delivery device having an elongated shaft extending along a longitudinal axis from a first end to a second end and comprising an inner surface defining a passageway, the first end comprising a first opening that is in communication with the passageway, the second end comprising a second opening that is in communication with the passageway, the shaft comprising a mixing portion between the first and second ends; a connector coupled to the first end and comprising first and second portions each extending from a central portion of the connector, the first portion comprising an inner surface defining a first lumen that is in communication with the first opening, the second portion comprising an inner surface defining a second lumen that is in communication with the first opening; a first tube disposed in the first lumen comprising an inner surface defining a first pathway configured for disposal of a first component of a bone cement; a second tube disposed in the second lumen comprising an inner surface defining a second pathway configured for disposal of a second component of the bone cement; a first plunger movably disposed in the first pathway and configured to move the first component from the first pathway and into the passageway; and a second plunger movably disposed in the second lumen and configured to move the second component from the second pathway and into the passageway.

In yet another exemplary embodiment, there is a method of filling a bone cavity with a bone cement, the method comprising: filling the bone cavity with the bone cement delivered from a bone mixing and delivery device having an elongated shaft extending along a longitudinal axis from a first end to a second end and comprising an inner surface defining a passageway, the first end comprising an adapter comprising an inner surface defining a first opening that is in communication with the passageway, the second end comprising a second opening that is in communication with the passageway, the shaft comprising a mixing portion between the first and second ends, the mixing portion comprising an inner surface having a helical configuration and defining a static vortex mixer; a connector comprising a central portion that that is coupled to the adapter, the central portion comprising an inner surface defining a channel that is in communication with the first opening, the central portion extending parallel to the longitudinal axis and comprising an aperture that is in communication with the channel, the connector comprising first and second ports that extend from the central portion, the first port comprising an inner surface defining a first lumen that is in communication with the channel, the second port comprising an inner surface defining a second lumen that is in communication with the channel, the first and second ports each extending at an acute angle relative to the longitudinal axis, the first and second ports extending at inverse angles relative to one another; the bone cement comprising separate first and second components that are each a flowable composition; a first cartridge coupled to the first port and a second cartridge coupled to the second port, the first cartridge comprising the first component and the second cartridge comprising the second component; a first syringe coupled to the first cartridge and configured to move the first component out of the first cartridge and into the channel; a second syringe coupled to the second cartridge and configured to move the second component out of the second cartridge and into the channel; and a plunger that extends through the aperture and into the channel to move the first and second components from the channel and into the passageway.

Accordingly, a bone cement mixing and delivery device is provided that comprises an elongated shaft extending along a longitudinal axis from a first end to a second end. The shaft comprises an inner surface defining a passageway. The first end comprises an adapter comprising an inner surface defining a first opening that is in communication with the passageway. The second end comprises a second opening that is in communication with the passageway. The shaft comprises a mixing portion between the first and second ends. A connector comprises a central portion that that is coupled to the adapter. The central portion comprises an inner surface defining a channel that is in communication with the first opening. The connector comprises first and second ports that extend from the central portion. The first port comprises an inner surface defining a first lumen that is in communication with the channel. The second port comprises an inner surface defining a second lumen that is in communication with the channel.

In one embodiment, there is a bone cement mixing and delivery device, comprising: an elongated shaft extending along a longitudinal axis from a first end to a second end and comprising an inner surface defining a passageway, the first end comprising an adapter comprising an inner surface defining a first opening that is in communication with the passageway, the second end comprising a second opening that is in communication with the passageway, the shaft comprising a mixing portion between the first and second ends; and a connector comprising a central portion that that is coupled to the adapter, the central portion comprising an inner surface defining a channel that is in communication with the first opening, the connector comprising first and second ports that extend from the central portion, the first port comprising an inner surface defining a first lumen that is in communication with the channel, the second port comprising an inner surface defining a second lumen that is in communication with the channel.

In another embodiment, there is a bone cement mixing and delivery device, comprising: an elongated shaft extending along a longitudinal axis from a first end to a second end and comprising an inner surface defining a passageway, the first end comprising a first opening that is in communication with the passageway, the second end comprising a second opening that is in communication with the passageway, the shaft comprising a mixing portion between the first and second ends; a connector coupled to the first end and comprising first and second portions each extending from a central portion of the connector, the first portion comprising an inner surface defining a first lumen that is in communication with the first opening, the second portion comprising an inner surface defining a second lumen that is in communication with the first opening; a first tube disposed in the first lumen comprising an inner surface defining a first pathway configured for disposal of a first component of a bone cement; a second tube disposed in the second lumen comprising an inner surface defining a second pathway configured for disposal of a second component of the bone cement; a first plunger movably disposed in the first pathway and configured to move the first component from the first pathway and into the passageway; and a second plunger movably disposed in the second lumen and configured to move the second component from the second pathway and into the passageway.

In yet another embodiment, there is a bone cement mixing and delivery device, comprising: an elongated shaft extending along a longitudinal axis from a first end to a second end and comprising an inner surface defining a passageway, the first end comprising an adapter comprising an inner surface defining a first opening that is in communication with the passageway, the second end comprising a second opening that is in communication with the passageway, the shaft comprising a mixing portion between the first and second ends, the mixing portion comprising an inner surface having a helical configuration and defining a static vortex mixer; a connector comprising a central portion that that is coupled to the adapter, the central portion comprising an inner surface defining a channel that is in communication with the first opening, the central portion extending parallel to the longitudinal axis and comprising an aperture that is in communication with the channel, the connector comprising first and second ports that extend from the central portion, the first port comprising an inner surface defining a first lumen that is in communication with the channel, the second port comprising an inner surface defining a second lumen that is in communication with the channel, the first and second ports each extending at an acute angle relative to the longitudinal axis, the first and second ports extending at inverse angles relative to one another; bone cement comprising separate first and second components that are each a flowable paste; a first cartridge coupled to the first port and a second cartridge coupled to the second port, the first cartridge comprising the first component and the second cartridge comprising the second component; a first syringe coupled to the first cartridge and configured to move the first component out of the first cartridge and into the channel; a second syringe coupled to the second cartridge and configured to move the second component out of the second cartridge and into the channel; and a plunger that extends through the aperture and into the channel to move the first and second components from the channel and into the passageway.

Other features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more readily apparent from the specific description accompanied by the following drawings, in which.

Like reference numerals indicate similar parts throughout the figures.

Figure 1:
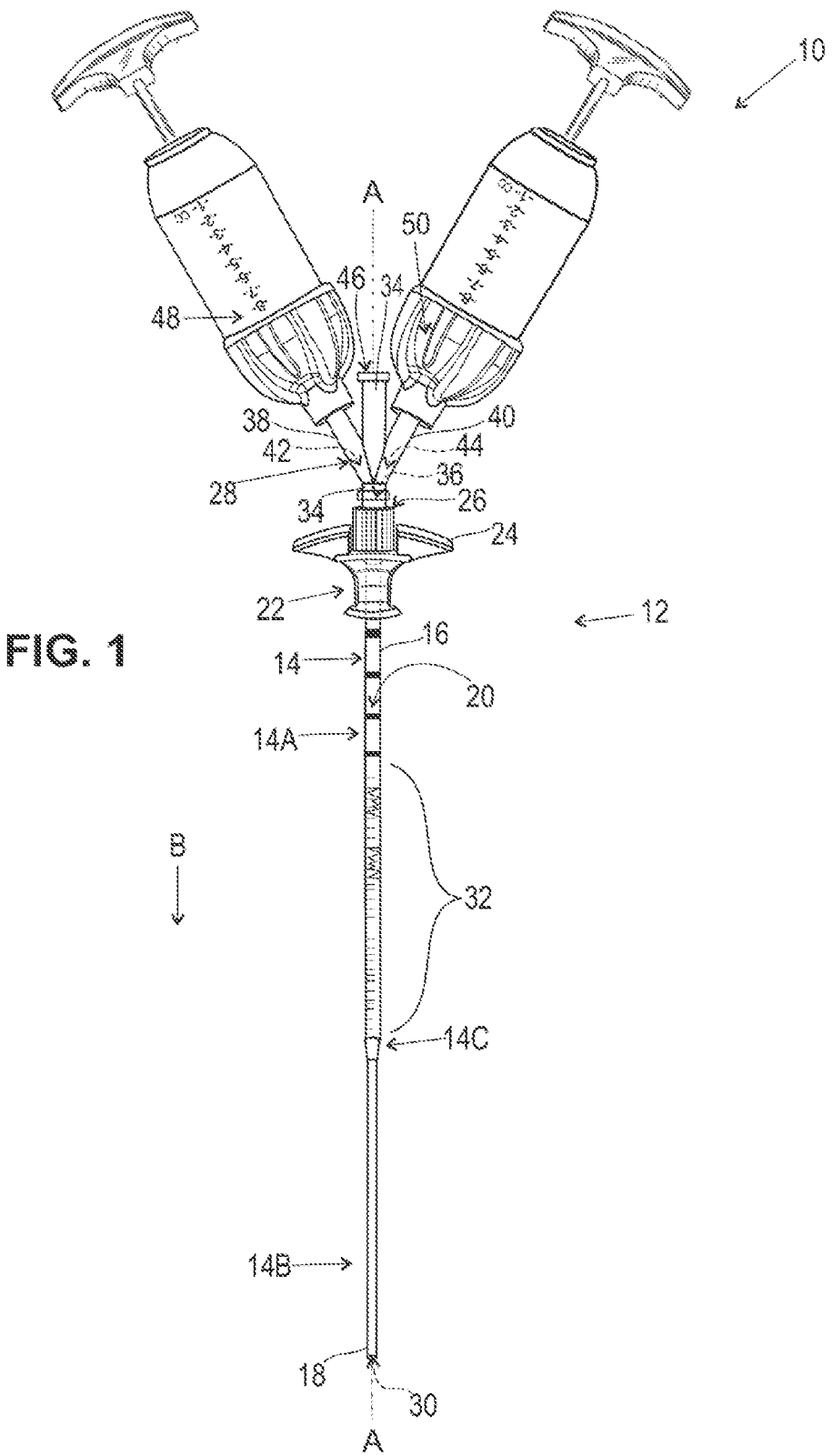
FIG. 1 is a side view, in part phantom, of one embodiment of components of a bone cement mixing and delivery device in accordance with the principles of the present disclosure.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

The exemplary embodiments of a bone cement mixing and delivery device and related methods are discussed in terms of medical devices for the treatment of skeletal injuries, disorders and repairs and more particularly, in terms of a bone cement mixing and delivery device and method for bone repair. It is envisioned that the device and method may be employed in applications such as correction of cracks, fissures, voids, e.g., due to osteoporosis or other diseases or injuries. In addition, the device and method may be employed with the placement of support structures or devices attached to or embedded within bone. For example, such structures may include pins, screws, replacement joints (e.g., of the hip, knee, shoulder), etc.

The bone cement mixing and delivery device provided allows mixing of flowable components and then delivery of the bone cement without transfer to a separate mixing device. The bone cement mixing and delivery device provided, in some embodiments, comprises a sealed delivery device that allows a portion of the flowable bone cement to be dispensed by controlled delivery in multiple doses to various target tissue sites without the need to reload new bone cement in the device. In some embodiments, the bone cement mixing and delivery device provided allows an unlimited working time for the physician to apply the bone cement to the target tissue site. The bone cement mixing and delivery device provided increases physician safety by decreasing the radiation exposure as the bone cement mixing and delivery device, in some embodiments, is a sufficient length (e.g., at least 48 inches) to keep the physician out of the fluoroscopic field.

In some embodiments, the bone cement mixing and delivery device is configured for mixing and delivery of a two-part, partially polymerized flowable cement paste. In some embodiments, the bone cement mixing and delivery device includes hydraulic cylinders that are used to provide pressure to both mix the cement within a bone cement mixing and delivery device and deliver the cement to a surgical site, such as, for example, a damaged and/or fractured bone. In some embodiments, the cement comprises a two-part flowable paste that allows for instant delivery and requires little user involvement.

Due to the viscosity of each of the two flowable bone cement components (e.g., pastes, gels, etc.) force is required to mix the two components into the cement and/or deliver the cement to a surgical site. In some embodiments, the bone cement mixing and delivery device includes a pressure syringe, such as, for example, a hydraulic pump (e.g., Kyphon Cement Delivery System CDS) that engages the components of the flowable bone cement. For example, the hydraulic pump (e.g., Kyphon Cement Delivery System CDS) engages 48 and 50 of FIG. 1 or 174 and 176 of FIG. 3 either directly or indirectly through a connector to create pressure that moves the components of the flowable bone cement into the mixing portion 32 to mix the two components into a cement and/or deliver the cement to a surgical site out of opening 30.

In some embodiments, the bone cement mixing and delivery device includes a Y adapter that includes two ports each having a hydraulic pump coupled thereto and a bone filler device (BFD) with a static mixer that is coupled to the Y adapter such that the cement can be directly injected into the target tissue site of the patient easily by utilizing high pressure capability of the hydraulic pumps. In some embodiments, the hydraulic pumps are configured to be independently operated. In some embodiments, the bone cement mixing and delivery device includes one or more in-line hydraulic valves, such as, for example, check valves, proportioning valves, flow divider valves, etc. In some embodiments, the bone cement mixing and delivery device includes one or more means to adjust mixture ratios of the two pastes, such as, for example, adjusting the diameter of cartridges that are coupled to the Y adapter and include the pastes, adjusting pressure delivered to each cartridge, adding in-line flow control valves, etc.

It is contemplated that one or all of the components of the bone cement mixing and delivery device may be disposable, peel-pack, pre-packed sterile devices. One or all of the components of the bone cement mixing and delivery device may be reusable. The bone cement mixing and delivery device may be configured as a kit with multiple sized and configured components.

In some embodiments, the bone cement mixing and delivery device may be configured to mix the two components of the bone cement according to a desired ratio based on weight to weight, volume to volume, weight to volume of each component (e.g. component 1 to component 2, ratio can be 1:1 wt. % to wt. %, vol % to vol %, or wt. % to vol %).

It is envisioned that the present disclosure may be employed to treat or repair bone injuries or disorders such as, for example, osteoporosis, joint replacement, fracture repairs, bone breaks, etc. It is contemplated that the present disclosure may be employed with other osteal and bone related applications, including those associated with diagnostics and therapeutics, such as the delivery of a therapeutic agents to a site for treatment or the delivery of radio opaque markers for tracking fluid once it is released into a patient. It is further contemplated that the disclosed bone cement delivery device and methods may be alternatively employed in a surgical treatment with a patient in a prone or supine position, and/or employs various surgical approaches, including anterior, posterior, posterior mid-line, direct lateral, postero-lateral, antero-lateral approaches, etc. in any body region. The device and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
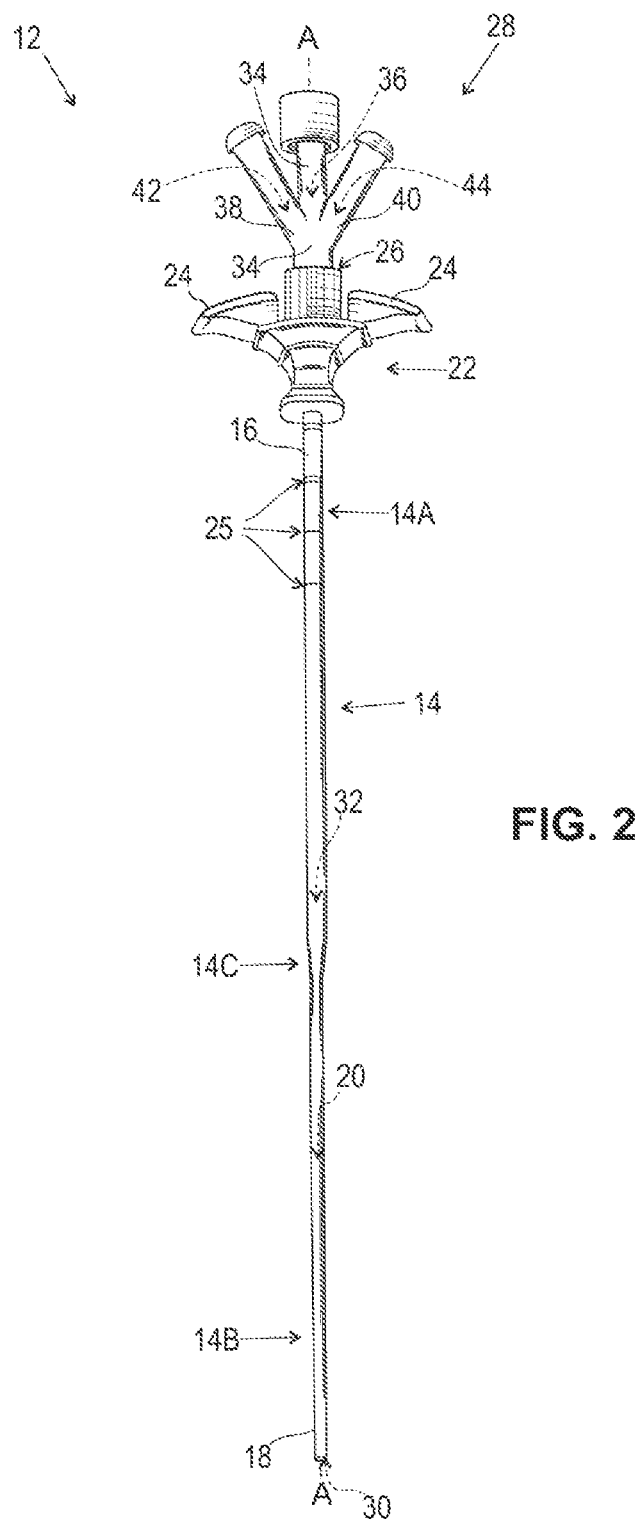
FIG. 2 is a side view of components of the device shown in FIG. 1.

The following discussion includes a description of the mixing and delivery device and related methods of employing the device in accordance with the principles of the present disclosure. Alternate embodiments are also disclosed. Reference will now be made in detail to the exemplary embodiments of the present disclosure, which are illustrated in the accompanying figures. Turning now to FIGS. 1 and 2, there are illustrated components of a bone cement mixing and delivery device 10 including a bone cement mixing and delivery device 12 in accordance with the principles of the present disclosure.

The components of device 10 can be fabricated from biologically acceptable materials suitable for medical applications, including metals, synthetic polymers, ceramics and bone material and/or their composites, depending on the particular application and/or preference of a medical practitioner. For example, the components of device 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, composites of metals and calcium-based ceramics, composites of PEEK and calcium based ceramics, and their combinations.

Various components of device 10 may have material composites, including the above materials, to achieve various desired characteristics such as strength, rigidity, elasticity, compliance, biomechanical performance, durability and radiolucency or imaging preference. The components of device 10, individually or collectively, may also be fabricated from a heterogeneous material such as a combination of two or more of the above-described materials. The components of device 10 may be monolithically formed, integrally connected or include fastening elements and/or instruments, as described herein.

Device 10 is employed, for example, with an open, mini-open or minimally invasive surgical technique to fill voids, provide patches, attach prosthetic devices, etc., or any other bone related repairs. Device 12 includes a bone filler device (BFD), such as, for example, an elongated shaft 14 extending along a longitudinal axis A from an end 16 to an end 18 that is opposite end 16. Shaft 14 comprises a portion 14A adjacent end 16 and a portion 14B adjacent end 18. Shaft 14 has a tapered portion 14C between portions 14A, 14B. Shaft 14 comprises an inner surface defining a passageway 20. Passageway 20 has a first diameter through portion 14A and a second diameter though portion 14B that is less than the first diameter. Shaft 14 has a length defined by the distance between end 16 and end 18. In some embodiments, the length of shaft 14 is sufficient to keep a medical practitioner out of the radiation area from the fluoroscope. In some embodiments, a cement delivery system such as a CDS gun available from Kyphon Sarl which contains a 4 inch tether can engage the device 10 at 48 of FIG. 1 that is a sufficient length (e.g., at least 48 inches) to keep the medical practitioner out of the radiation area generated by the fluoroscope. In some embodiments, the length of shaft 14 is sufficient to keep a medical practitioner a sufficient distance from a radiation source, such as, for example, a fluoroscope, when end 18 is positioned adjacent a surgical site, such as, for example a damaged or fractured bone, such as, for example, one or more vertebrae.

In some embodiments, shaft 14 comprises a rigid material such that shaft 14 cannot be bent without breaking. In some embodiments, shaft 14 comprises a flexible material such that shaft 14 can bent without breaking. In some embodiments, shaft 14 comprises a transparent and/or translucent material that permits a medical practitioner to view materials disposed within passageway 20 to determine whether components of a bone cement are adequately mixed, for example, as will be discussed in greater detail hereinbelow. In some embodiments, end 18 defines a blunt tip of shaft 14 that is configured to prevent penetration of tissue and/or other injury to tissue. In some embodiments, end 18 is rounded to prevent penetration of tissue and/or other injury to tissue. In some embodiments, passageway 20 may be disposed at alternate orientations, relative to axis A, such as, for example, parallel, transverse, perpendicular and/or other angular orientations such as acute or obtuse, co-axial and/or may be offset or staggered. In some embodiments, an outer surface of shaft 14 comprises a series of graduated markings 25 configured to indicate the depth shaft 14 has been inserted into a surgical site or pathway, for example.

End 16 comprises an adapter 22 comprising a pair of arms 24 that extend parallel to one another and are configured for gripping by a medical practitioner to selectively position and/or move device 12. In some embodiments, adapter 22 is fixed to shaft 14. Adapter 22 comprises an inner surface defining an opening 26 that is in communication with passageway 20. In some embodiments, opening 26 includes an internal thread form configured to engage an external thread form of a connector 28 to couple connector 28 to adapter 22, as will be discussed in greater detail hereinbelow. End 18 comprises an opening 30 that is in communication with passageway 20. Shaft 14 comprises a mixing portion 32 between ends 16 and 18. The inner surface of shaft 14 that defines passageway 20 has a helical configuration through portion 32 to define a static vortex mixer configured to mix two separate flowable components of the bone cement BC, as will be discussed in greater detail hereinbelow. This static vortex mixer can be embedded in the elongated shaft to enhance mixing of the two components of the bone cement.

The inner surface of shaft 14 that defines passageway 20 is integrally formed and/or monolithic with shaft 14 such that the static vortex mixer defined by the helical portion of passageway 20 is permanently fixed relative to shaft 14. In some embodiments, portion 32 may be variously configured and can have a configuration that adequately mixes the first and second components of bone cement BC as the first and second components of bone cement BC passes through portion 32.

Due to the configuration of shaft 14 discussed above, opening 26 has a width or diameter that is greater than that of opening 30. In some embodiments, opening 26 and/or opening 30 may have various cross section configurations, such as, for example, oval, oblong, triangular, rectangular, square, polygonal, irregular, uniform, non-uniform, variable, tubular and/or tapered. In some embodiments, opening 26 and/or opening 30 may be disposed at alternate orientations, relative to axis A, such as, for example, parallel, transverse, perpendicular and/or other angular orientations such as acute or obtuse, co-axial and/or may be offset or staggered. In some embodiments, adapter 22 comprises a material that is different than the material that forms shaft 14. In some embodiments, adapter 22 comprises molded plastic and shaft 14 comprises metal. In some embodiments, connector 28 can be variously connected with adapter 22, such as, for example, monolithic, integral connection, frictional engagement, threaded engagement, mutual grooves, screws, adhesive, nails, barbs and/or raised element.

Connector 28 comprises a central portion 34 that that is coupled to adapter 22. As discussed above, portion 34 comprises an external thread form that engages an internal thread form of opening 26 to couple connector 28 with adapter 22. Portion 34 comprises an inner surface defining a channel 36 that is in communication with opening 26. Connector 28 comprises ports 38, 40 that extend from portion 34. Port 38 comprises an inner surface defining a lumen 42 that is in communication with channel 36. Port 40 comprises an inner surface defining a lumen 44 that is in communication with channel 36. Port 38 and port 40 each extend at an acute angle relative to axis A. In some embodiments, ports 38 and 40 extend at inverse angles relative to one another. Portion 34 extends parallel to axis A and comprises an aperture 46 that is in communication with channel 36. It will be understood by those of ordinary skill in the art that portion 34 is optional and, in some embodiments, portion 34 is not necessary.

In some embodiments, channel 36, lumen 42, lumen 44 and/or aperture 46 may have various cross section configurations, such as, for example, circular, oval, oblong, triangular, rectangular, square, polygonal, irregular, uniform, non-uniform, variable, tubular and/or tapered. In some embodiments, connector 28 comprises a cap 45 that covers aperture 46 when aperture 46 is not in use, as will be discussed in greater detail herein below. In some embodiments, connector 28 can be variously connected with adapter 22, and/or cap 45 can be variously connected with connector 28, such as, for example, monolithic, integral connection, frictional engagement, threaded engagement, mutual grooves, screws, adhesive, nails, barbs and/or raised element.

In some embodiments, a cartridge 48 is coupled to port 38 and a cartridge 50 substantially similar to cartridge 48 is coupled to port 40. In some embodiments, port 38 comprises an external thread form that engages an internal thread form of cartridge 48 to couple cartridge 48 to port 38 and port 40 comprises an external thread form that engages an internal thread form of cartridge 50 to couple cartridge 50 to port 40. Cartridge 48 includes a cavity having a first flowable paste component of cement BC disposed therein and cartridge 50 includes a cavity having a second flowable paste component of cement BC disposed therein. In some embodiments, cartridge 48 can be variously connected with port 38 and/or cartridge 50 can be variously connected with port 40, such as, for example, monolithic, integral connection, frictional engagement, threaded engagement, mutual grooves, screws, adhesive, nails, barbs and/or raised element.

In some embodiments, bone cement BC comprises a poly(methyl methacrylate) (PMMA); methyl methacrylate (MMA); calcium phosphate; a resorbable polymer, such as, for example, PLA, PGA or combinations thereof; a resorbable polymer with allograft, such as, for example, particles or fibers of mineralized bone; Plexur® sold by Osteotech, Inc., and combinations thereof. In some embodiments, bone cement BC is a high viscosity bone cement. In some embodiments, bone cement BC has a viscosity that is at least 500 Pascal-sec (Pa-s) to infiltrate a medical site and prevent any migration of bone cement BC during medical procedures. In some embodiments, bone cement BC has a viscosity that is at least 600 Pa-s. In some embodiments, bone cement BC has a viscosity that is at least 800 Pa-s. In some embodiments, bone cement BC has a viscosity that is at least 1,000 Pa-s. In some embodiments, bone cement BC comprises a polymerization accelerator.

In some embodiments, a syringe is coupled to cartridge 48 and is configured to move the first component of bone cement BC out of the cartridge 48 and into channel 36 and another syringe is coupled to cartridge 50 and is configured to move the second component of bone cement BC out of cartridge 50 and into channel 36. In some embodiments, the syringes are hydraulic pumps available from Kyphon Sarl as part of Kyphon's Cement Delivery System (CDS). In some embodiments, the syringes are coupled directly to cartridges 48, 50. In some embodiments, the syringes are coupled to cartridges 48, 50 via tubing having a material, such as, for example, a hydraulic fluid disposed therein such that one of the syringes moves the hydraulic fluid through one of the tubing such that the hydraulic fluid applies a force upon a piston movably positioned in cartridge 48 such that the piston moves the first component of bone cement BC out of cartridge 48 and into lumen 42 and another one of the syringes moves the hydraulic fluid through the other tubing such that the hydraulic fluid applies a force upon a piston movably positioned in cartridge 50 such that the piston moves the second component of bone cement BC out of cartridge 50 and into lumen 44. The first component of bone cement BC moves from lumen 42 into channel 36 and the second component of bone cement BC moves from lumen 44 into channel 36.

In some embodiments, device 10 includes a plunger movably positioned in channel 36. In some embodiments, the plunger is slidably disposed in channel 36 such that a distal end of the plunger engages the first and second components of bone cement BC that are disposed in channel 36. Moving the plunger along axis A in the direction shown by arrow B thus moves the first and second components of bone cement BC from channel 36, through opening 26 and into portion 14A. Moving the plunger along axis A further in the direction shown by arrow B moves the first and second components of bone cement BC from portion 14A into portion 32 where the first and second components of bone cement BC are mixed with one another in the static mixer defined by portion 32. Bone cement BC is moved from portion 32 and into portion 14B, where bone cement BC is fully mixed. Pressure created by the syringes and/or the plunger moves fully mixed bone cement BC from portion 14B out of shaft 14 via opening 30 to deliver fully mixed bone cement BC to a surgical site, such as, for example, a damaged or fractured bone. In some embodiments, the hydraulic fluid is saline. The hydraulic fluid does not contact the components of the bone cement.

In assembly, operation and use, device 10 is employed with a surgical procedure, such as, for a treatment of bone injuries, to provide bone repairs, to strengthen or rebuild bones, etc. It is contemplated that one or all of the components of device 10 can be delivered as a pre-assembled device or can be assembled in situ. Device 10 may be completely or partially revised, removed or replaced.

Device 10 and accessories thereof, described above, can be employed during a surgical procedure for dispensing bone cement BC. In use, a medical practitioner obtains access to a surgical site including a bone, such as, for example, a vertebra in need of repair, in any appropriate manner, such as, for example, through incision and retraction of tissues. It is envisioned that device 10 can be used in any existing surgical method or technique including open surgery, mini-open surgery, minimally invasive surgery and percutaneous surgical implantation, whereby the bone is accessed through a mini-incision, or sleeve that provides a protected passageway to the area. In some embodiments, the void in the bone to be filled is created using an inflatable bone tamp by inserting a balloon of the inflatable bone tamp into bone, such as, for example, cancellous bone and expanding the balloon to create the void. In some embodiments, the void in the bone to be filled is created naturally and/or by injury to the patient. In some embodiments, the void in the bone is created during part of a surgical procedure.

An incision is made in the body of a patient and a cutting instrument creates a surgical pathway for insertion of components of device 10, such as, for example, shaft 14. A preparation instrument can be employed to prepare tissue surfaces of the bone, as well as for aspiration and irrigation of a surgical region according to the requirements of a particular surgical application. In some embodiments, shaft 14 is inserted into the surgical pathway such that opening 30 is positioned adjacent hole(s), fracture(s), void(s), depression(s), etc. in the bone that the medical practitioner desires to fill, at least partly, with bone cement BC to maintain or improve the bone's structural integrity. Significantly, the length of shaft is sufficient to position a medical practitioner out of the radiation area from the fluoroscope. In some embodiments, a cement delivery system such as a CDS gun available from Kyphon Sarl which contains a 4 inch tether can engage the device 10 at 48 of FIG. 1 that is a sufficient length (e.g., at least 48 inches) to keep the medical practitioner out of the radiation area generated by the fluoroscope. That is, the length of shaft 14 is sufficient to keep a medical practitioner a sufficient distance from a radiation source, such as, for example, a fluoroscope, when end 18 is positioned adjacent a surgical site, such as, for example a damaged or fractured bone, such as, for example, one or more vertebrae.

The syringe coupled to cartridge 48 is actuated to move the hydraulic fluid in the syringe coupled to cartridge 48 through one of the tubing such that the hydraulic fluid applies a force upon the piston movably positioned in cartridge 48 such that the piston moves the first component of bone cement BC out of cartridge 48 and into lumen 42. The syringe coupled to cartridge 50 is actuated to move the hydraulic fluid through the other tubing such that the hydraulic fluid applies a force upon the piston movably positioned in cartridge 50 such that the piston moves the second component of bone cement BC out of cartridge 50 and into lumen 44. The first component of bone cement BC moves from lumen 42 into channel 36 and the second component of bone cement BC moves from lumen 44 into channel 36.

Cap 45 is removed from portion 34 such that the plunger is inserted through aperture 46 and into channel 36. The plunger is translated within channel 36 along axis A in the direction shown by arrow B to move the first and second components of bone cement BC from channel 36, through opening 26 and into portion 14A. The plunger is further moved along axis A in the direction shown by arrow B to move the first and second components of bone cement BC from portion 14A into portion 14C. In some embodiments, the plunger is stopped from translating within passageway 20 along axis A before the plunger enters portion 32. That is the plunger does not enter portion 32. As the pressure created by the syringes and/or the plunger moves fully mixed bone cement BC move through portion 32, the first and second components of bone cement BC are mixed with one another in the static mixer defined by portion 32. Pressure created by the syringes and/or the plunger moves fully mixed bone cement BC from portion 32 and into portion 14B. Pressure created by the syringes and/or the plunger moves fully mixed bone cement BC from portion 14B out of shaft 14 via opening 30 to deliver fully mixed bone cement BC to a surgical site, such as, for example, a damaged or fractured bone. In some embodiments, bone cement BC is delivered into the fracture or void in the bone to at least partially fill the fracture or void. In some embodiments, bone cement BC is allowed to cure within the facture or void.

In some embodiments, the first and second components of bone cement BC are configured to be mixed with one another such that the first component of bone cement BC is mixed with the second component of bone cement BC in a selected ratio. In some embodiments, the selected ratio is 1:1. In some embodiments the 1:1 ratio includes a first amount of the first component of bone cement BC being mixed with the same amount or substantially the same amount of the second component of bone cement BC. In some embodiments the relative amounts of the first and second components of bone cement BC are in mass, volume, weight or a combination of the same. In some embodiments, to mix the first and second components of bone cement BC in a 1:1 ratio, the widths and/or diameters of cartridges 48, 50 are the same. In some embodiments, to mix the first and second components of bone cement BC in a 1:1 ratio, the amount of pressure provided to each of cartridges 48, 50 is the same. In some embodiments, to mix the first and second components of bone cement BC in a 1:1 ratio, an in-line flow control valve is provided to equalize the amount of pressure in each of cartridges 48, 50 and/or each of lumens 42, 44. In some embodiments, the syringes are moved relative to cartridges 48, 50 simultaneously and at approximately the same rate such that the same amount or substantially the same amount of the first component of bone cement BC moves from cartridge 48, through lumen 42 and into passageway 20 as the amount of the second component of bone cement BC that moves from cartridge 50, through lumen 44 and into passageway 20.

It will be understood that the other ratios of components can be used and the device can be calibrated to deliver the flowable components at other ratios (e.g., 0.5, 0.25, 0.1 to 1) based on weight, volume and flowability of the components.

In one embodiment, device 10 may also deliver an agent, which may be mixed in the bone cement BC or delivered separately. It is envisioned that the agent may include bone growth promoting material. In some embodiments, cartridge 48 and/or cartridge 50 are pre-loaded with the agent before the first and second components of bone cement BC are loaded into cartridge 48 and/or cartridge 50. Device 12 then is used to expel the agent through opening 30 in the same manner as bone cement BC is expelled from opening 30, discussed above, such that the agent penetrates at least a portion of the bone fracture or void. Device 12 is then removed from the surgical site through the surgical pathway and the first and second components of bone cement BC are loaded into cartridge 48 and/or cartridge 50. Fully mixed bone cement BC is then expelled from opening 30 in the manner discussed above. In some embodiments, device 12 is removed from the surgical pathway after the bone is at least partially filled with bone cement. Device 12 is then reinserted into the surgical pathway such that opening 30 is positioned adjacent the at least partially filled bone. Device 12 then is used to expel the agent through opening 30 in the same manner as bone cement BC is expelled from opening 30 in the manner discussed above.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of correction device 10 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair bone deterioration or damage, with the aid of the device 10. Upon completion of the procedure, the surgical instruments and assemblies are removed and the incision is closed.

Figure 3:
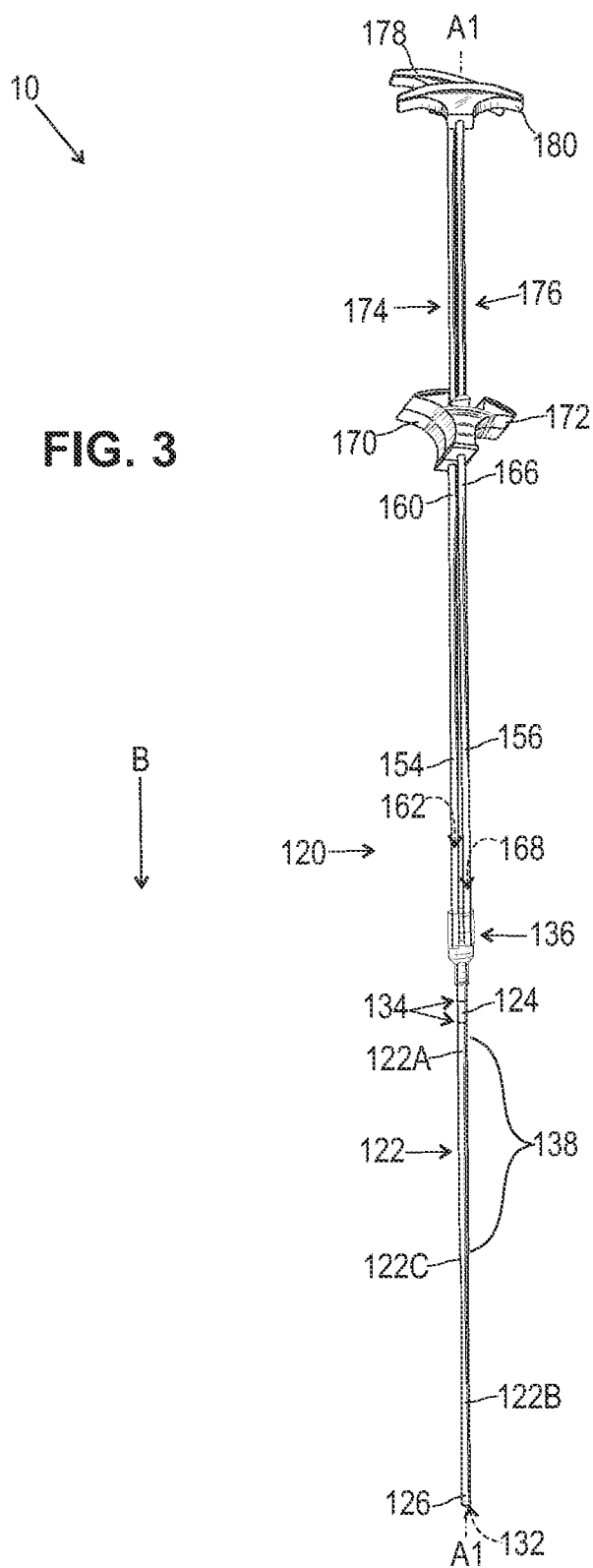
FIG. 3 is a side view of one embodiment of components of a bone cement mixing and delivery device in accordance with the principles of the present disclosure.
Figure 4:
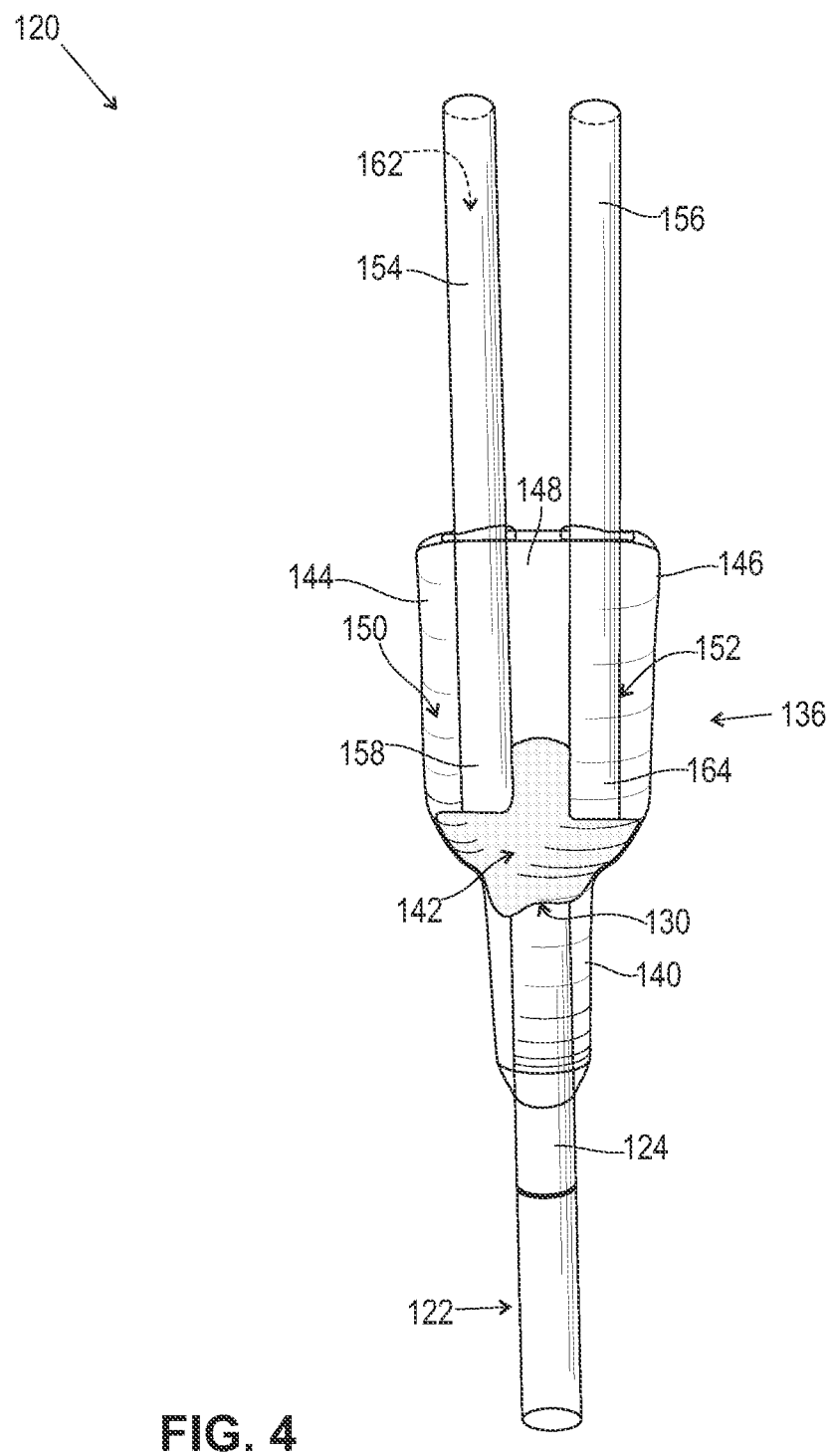
FIG. 4 is an enlarged side view of components of the device shown in FIG. 3.
Figure 5:
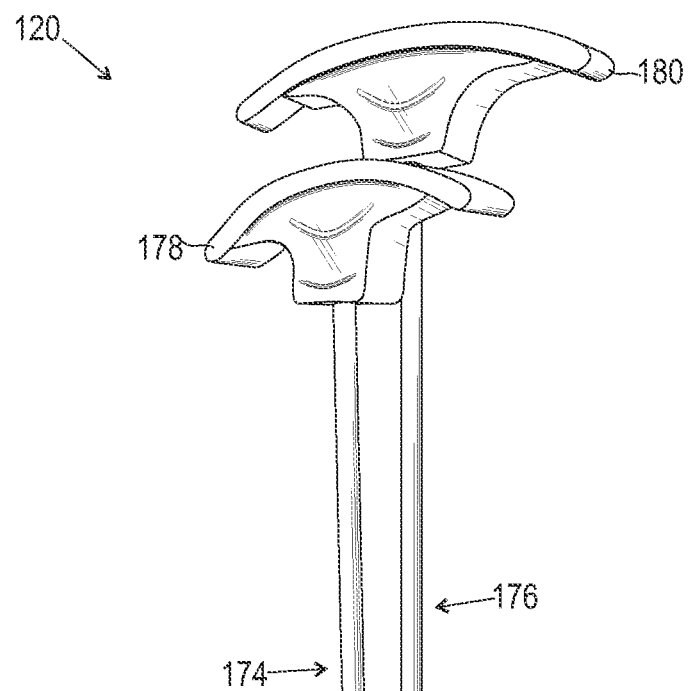
FIG. 5 is side view of components of the device shown in FIG. 3.

Turning now to FIGS. 3-5, device 10 includes a bone cement mixing and delivery device 120 in accordance with the principles of the present disclosure. Device 120 comprises a bone filler device (BFD), such as, for example, an elongated shaft 122 extending along a longitudinal axis A1 from an end 124 to an end 126 opposite end 124.

Shaft 122 comprises a portion 122A adjacent end 124 and a portion 122B adjacent end 126. Portion 122A has a width or diameter that is greater than that of portion 122B. Shaft 122 has a tapered portion 122C between portions 122A, 122B. Shaft 122 comprises an inner surface defining a passageway 138. Passageway 138 has a first diameter through portion 122A and a second diameter though portion 122B that is less than the first diameter. Shaft 122 has a length defined by the distance between end 124 and end 126. In some embodiments, the length of shaft 122 is sufficient to keep a medical practitioner out of the radiation area from the fluoroscope. That is, the length of shaft 122 is sufficient to keep a medical practitioner a sufficient distance from a radiation source, such as, for example, a fluoroscope, when end 126 is positioned adjacent a surgical site, such as, for example a damaged or fractured bone, such as, for example, one or more vertebrae. End 124 comprises an opening 130 that is in communication with passageway 138. End 126 comprises an opening 132 that is in communication with passageway 138.

In some embodiments, shaft 122 comprises a rigid material such that shaft 122 cannot be bent without breaking. In some embodiments, shaft 122 comprises a flexible material such that shaft 122 can bent without breaking. In some embodiments, shaft 122 comprises a transparent and/or translucent material that permits a medical practitioner to view materials disposed within passageway 138 to determine whether components of a bone cement are adequately mixed, for example, as will be discussed in greater detail herein below. Shaft 122 comprises a mixing portion between ends 124, 126. The inner surface of shaft 122 that defines passageway 138 has a helical configuration through portion to define a static vortex mixer configured to mix the first and second components of bone cement BC, discussed above. The inner surface of shaft 122 that defines passageway 138 is integrally formed and/or monolithic with shaft 122 such that the static vortex mixer defined by the helical portion of passageway 138 is permanently fixed relative to shaft 122. In some embodiments, portion may be variously configured and can have an configuration that adequately mixes the first and second components of bone cement BC as the first and second components of bone cement BC passes through portion.

In some embodiments, end 126 defines a blunt tip of shaft 122 that is configured to prevent penetration of tissue and/or other injury to tissue. In some embodiments, end 126 is rounded to prevent penetration of tissue and/or other injury to tissue. In some embodiments, passageway 138 may be disposed at alternate orientations, relative to axis A1, such as, for example, parallel, transverse, perpendicular and/or other angular orientations such as acute or obtuse, co-axial and/or may be offset or staggered. In some embodiments, an outer surface of shaft 122 comprises a series of graduated markings 134 configured to indicate the depth shaft 122 has been inserted into a surgical site or pathway, for example.

A connector 136 is fixed to shaft 122. Connector 136 comprises a central portion 140 including an inner surface defining a conduit 142 that is in communication with opening 130. Connector 136 includes a portion 144 extending from portion 140 and a portion 146 extending from portion 140. Portions 144, 146 each extend parallel to axis A1. Portion 144 is spaced apart from portion 146 by a wall 148. Portion 144 comprises an inner surface defining a lumen 150 that is in communication with conduit 142 and opening 130. Portion 146 comprises an inner surface defining a lumen 152 that is in communication with conduit 142 and opening 130. In some embodiments, connector 136 comprises a transparent and/or translucent material configured to allow a medical practitioner to properly insert shaft 122 into portion 140, a tube 154 into lumen 150 and a tube 156 into lumen 152. In some embodiments, they may all be affixed together for example, by glue, adhesive or be formed as one piece. In some embodiments, lumen 150 may be disposed at alternate orientations, relative to axis A1 and/or lumen 152, such as, for example, transverse, perpendicular and/or other angular orientations such as acute or obtuse, co-axial and/or may be offset or staggered. In some embodiments, connector 136 comprises an elastomeric material such that lumen 150 and/or lumen 152 can be stretched to increase a width or diameter thereof for insertion of one of tubes 154, 156 and then the width or diameter of lumen 150 and/or lumen 152 decreases such that inner surfaces of connector 136 that define lumens 150, 152 engage outer surfaces of tubes 154, 156 to fix tubes 154, 156 relative to connector 136. In some embodiments, tubes 154, 156 can be variously connected with connector 136, such as, for example, monolithic, integral connection, frictional engagement, threaded engagement, mutual grooves, screws, adhesive, nails, barbs and/or raised element.

Tube 154 comprises an end 158 positioned in lumen 150 and an end 160 opposite end 158. Tube 154 comprises an inner surface defining a pathway 162 configured for disposal of the first component of bone cement BC. Tube 156 comprises an end 164 positioned in lumen 152 and an end 166 opposite end 164. Tube 156 comprises an inner surface defining a pathway 168 configured for disposal of the second component of bone cement BC. In some embodiments, pathway 162 and/or pathway 168 each have a uniform diameter and a cylindrical cross sectional configuration. End 160 comprises an adapter 170 and end 166 comprises an adapter 172.

A plunger 174 is movably disposed in pathway 162 and configured to move the first component of bone cement BC from pathway 162, through opening 130 and into passageway 138. A plunger 174 is movably disposed in pathway 162 and configured to move the first component of bone cement BC from pathway 162, through opening 130 and into passageway 138. A proximal end of plunger 174 comprises a handle 178 and a proximal end of plunger 176 comprises a handle 180.

An incision is made in the body of a patient and a cutting instrument creates a surgical pathway for insertion of components of device 10, such as, for example, shaft 122. A preparation instrument can be employed to prepare tissue surfaces of the bone, as well as for aspiration and irrigation of a surgical region according to the requirements of a particular surgical application. In some embodiments, shaft 122 is inserted into the surgical pathway such that opening 132 is positioned adjacent hole(s), fracture(s), void(s), depression(s), etc. in the bone that the medical practitioner desires to fill, at least partly, with bone cement BC to maintain or improve the bone's structural integrity. Significantly, the length of shaft is sufficient to position a medical practitioner out of the radiation area from the fluoroscope. That is, the length of shaft 122 is sufficient to keep a medical practitioner a sufficient distance from a radiation source, such as, for example, a fluoroscope, when end 126 is positioned adjacent a surgical site, such as, for example a damaged or fractured bone, such as, for example, one or more vertebrae.

Portion 140 is fitted over end 124 to couple shaft 122 with connector 136. End 158 is positioned within lumen 150 and end 164 is positioned within lumen 152. The first component of bone cement BC is loaded into pathway 162 and the second component of bone cement BC is loaded into pathway 168. Due to the viscosity of the flowable components that make up the first and second components of bone cement BC, the first component of bone cement BC does not move from pathway 162, through opening 130 and into passageway 138 without the application of additional pressure and/or force. Likewise, the second component of bone cement BC does not move from pathway 168, through opening 130 and into passageway 138 without the application of additional pressure and/or force.

In order to move the first component of bone cement BC from pathway 162, through opening 130 and into passageway 138 and the second component of bone cement BC from pathway 168, through opening 130 and into passageway 138, plunger 174 is inserted into pathway 162 and plunger 176 is inserted into pathway 168. Plunger 174 is moved relative to shaft 122 and/or tube 154 in the direction shown by arrow B such that the first component of bone cement BC moves from pathway 162, through opening 130 and into passageway 138. Plunger 176 is moved relative to shaft 122 and/or tube 156 in the direction shown by arrow B such that the second component of bone cement BC moves from pathway 168, through opening 130 and into passageway 138. In some embodiments, plungers 174, 176 are moved relative to tubes 154, 156 and/or shaft 122 simultaneously and at approximately the same rate such that the same amount or substantially the same amount of the first component of bone cement BC moves from pathway 162, through opening 130 and into passageway 138 as the amount of the second component of bone cement BC that moves from pathway 168, through opening 130 and into passageway 138.

In some embodiments, plunger 174 is moved relative to shaft 122 and/or tube 154 in the direction shown by arrow B until an internal thread form in handle 178 engages an external thread form of adapter 170 and plunger 176 is moved relative to shaft 122 and/or tube 156 in the direction shown by arrow B until an internal thread form in handle 180 engages an external thread form of adapter 172. This fixes plunger 174 relative to tube 154 and/or shaft 122 and fixes plunger 176 relative to tube 156 and/or shaft 122. Moving plungers 174, 176 in the direction shown by arrow B until handles 178, 180 engage adapters 170, 172 causes the first and components of bone cement BC to move through portion such that the first and second components of bone cement BC become mixed. The pressure and/or force created by moving plungers 174, 176 in the direction shown by arrow B causes fully mixed bone cement BC to move into portion 122B and out of opening 132 for delivery to the surgical site, such as, for example, a damaged or fractured bone. In some embodiments, bone cement BC is delivered into the fracture or void in the bone to at least partially fill the fracture or void. In some embodiments, bone cement BC is allowed to cure within the facture or void.

In some embodiments, the first and second components of bone cement BC are configured to be mixed with one another such that the first component of bone cement BC is mixed with the second component of bone cement BC in a selected ratio. In some embodiments, the selected ratio is 1:1. In some embodiments, to mix the first and second components of bone cement BC in a 1:1 ratio, the widths and/or diameters of pathways 162, 168 are the same. In some embodiments, to mix the first and second components of bone cement BC in a 1:1 ratio, the amount of pressure provided/created from/by moving plungers 174, 176 in the direction shown by arrow B is the same. In some embodiments, to mix the first and second components of bone cement BC in a 1:1 ratio, an in-line flow control valve is provided to equalize the amount of pressure in each of pathways 162, 168. In some embodiments the 1:1 ratio includes a first amount of the first component of bone cement BC being mixed with the same amount or substantially the same amount of the second component of bone cement BC. In some embodiments the relative amounts of the first and second components of bone cement BC are in mass, volume, weight or a combination of the same.

In one embodiment, device 10 may also deliver an agent, which may be mixed in the bone cement BC or delivered separately. It is envisioned that the agent may include bone growth promoting material. In some embodiments, pathway 162 and/or pathway 168 are pre-loaded with the agent before the first and second components of bone cement BC are loaded into pathway 162 and/or pathway 168. Device 120 then is used to expel the agent through opening 132 in the same manner as bone cement BC is expelled from opening 132, discussed above, such that the agent penetrates at least a portion of the bone fracture or void. Device 120 is then removed from the surgical site through the surgical pathway and the first and second components of bone cement BC are loaded into pathway 162 and/or pathway 168. Fully mixed bone cement BC is then expelled from opening 132 in the manner discussed above. In some embodiments, device 120 is removed from the surgical pathway after the bone is at least partially filled with bone cement. Device 120 is then reinserted into the surgical pathway such that opening 132 is positioned adjacent the at least partially filled bone. Device 120 then is used to expel the agent through opening 132 in the same manner as bone cement BC is expelled from opening 132.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of correction device 10 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair bone deterioration or damage, with the aid of the device 10. Upon completion of the procedure, the surgical instruments and assemblies are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method of filling a bone cavity with a bone cement, the method comprising: filling the bone cavity with the bone cement delivered from a bone mixing and delivery device having an elongated shaft extending along a longitudinal axis from a first end to a second end and comprising an inner surface defining a passageway, the first end comprising a first opening that is in communication with the passageway, the second end comprising a second opening that is in communication with the passageway, the shaft comprising a mixing portion between the first and second ends; a connector coupled to the first end and comprising first and second portions each extending from a central portion of the connector, the first portion comprising an inner surface defining a first lumen that is in communication with the first opening, the second portion comprising an inner surface defining a second lumen that is in communication with the first opening; a first tube disposed in the first lumen comprising an inner surface defining a first pathway configured for disposal of a first component of a bone cement; a second tube disposed in the second lumen comprising an inner surface defining a second pathway configured for disposal of a second component of the bone cement; a first plunger movably disposed in the first pathway and configured to move the first component from the first pathway and into the passageway; and a second plunger movably disposed in the second lumen and configured to move the second component from the second pathway and into the passageway.

2. A method as recited in claim 1, wherein the first and second lumens each extend at an acute angle relative to the longitudinal axis.

3. A method as recited in claim 2, wherein the first and second lumens extend at inverse angles relative to one another.

4. A method as recited in claim 1, wherein the second opening is coaxial with the longitudinal axis.

5. A method as recited in claim 1, wherein an outer surface of the shaft comprises a series of graduated markings configured to indicate insertion depth.

6. A method as recited in claim 1, wherein the shaft has a length defined by a distance between the first and second ends, the length of the shaft being sufficient to keep a physician a sufficient distance from a radiation source when the second end is positioned adjacent a surgical site.

7. A method as recited in claim 1, wherein the second end comprises a blunt tip.

8. A method as recited in claim 1, wherein the first and second tubes extend parallel to one another.

9. A method as recited in claim 1, wherein the mixing portion comprises an inner surface having a helical configuration and defining a static vortex mixer.

10. A method as recited in claim 9, wherein the first and second components of the bone cement are flowable pastes.

11. A method of filling a bone cavity with a bone cement, the method comprising: filling the bone cavity with the bone cement delivered from a bone mixing and delivery device having an elongated shaft extending along a longitudinal axis from a first end to a second end and comprising an inner surface defining a passageway, the first end comprising an adapter comprising an inner surface defining a first opening that is in communication with the passageway, the second end comprising a second opening that is in communication with the passageway, the shaft comprising a mixing portion between the first and second ends, the mixing portion comprising an inner surface having a helical configuration and defining a static vortex mixer; a connector comprising a central portion that is coupled to the adapter, the central portion comprising an inner surface defining a channel that is in communication with the first opening, the central portion extending parallel to the longitudinal axis and comprising an aperture that is in communication with the channel, the connector comprising first and second ports that extend from the central portion, the first port comprising an inner surface defining a first lumen that is in communication with the channel, the second port comprising an inner surface defining a second lumen that is in communication with the channel, the first and second ports each extending at an acute angle relative to the longitudinal axis, the first and second ports extending at inverse angles relative to one another; the bone cement comprising separate first and second components that are each a flowable composition; a first cartridge coupled to the first port and a second cartridge coupled to the second port, the first cartridge comprising the first component and the second cartridge comprising the second component; a first syringe coupled to the first cartridge and configured to move the first component out of the first cartridge and into the channel; a second syringe coupled to the second cartridge and configured to move the second component out of the second cartridge and into the channel; and a plunger that extends through the aperture and into the channel to move the first and second components from the channel and into the passageway.

12. A method as recited in claim 11, wherein the first and second components of the bone cement are pastes.

13. A method as recited in claim 11, wherein the first port comprises an external thread form that engages an internal thread form of the first cartridge to couple the first cartridge to the first port and the second port comprises an external thread form that engages an internal thread form of the second cartridge to couple the second cartridge to the second port.

14. A method as recited in claim 11, wherein the adapter comprises a first thread form that engages a second thread form of the central portion to couple the connector to the adapter.

* * * * *